United States Patent
Weber et al.

(10) Patent No.: US 7,601,678 B2
(45) Date of Patent: Oct. 13, 2009

(54) WASHING AND CLEANING AGENTS COMPRISING FINE MICROPARTICLES WITH CLEANING AGENT COMPONENTS

(75) Inventors: Henriette Weber, Wien/Österreich (DE); Wilfried Raehse, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 10/637,071

(22) Filed: Aug. 7, 2003

(65) Prior Publication Data

US 2004/0029765 A1 Feb. 12, 2004

Related U.S. Application Data

(63) Continuation of application No. PCT/EP02/00881, filed on Jan. 29, 2002.

(30) Foreign Application Priority Data

Feb. 7, 2001 (DE) .................... 101 05 801

(51) Int. Cl.
*C11D 17/00* (2006.01)
*C11D 17/06* (2006.01)

(52) U.S. Cl. ............. 510/444; 510/445; 510/446; 510/451; 510/108; 510/224; 510/298; 510/438; 510/474; 510/511

(58) Field of Classification Search ............ 510/444, 510/445, 446, 451, 224, 298, 108, 438, 474, 510/511
See application file for complete search history.

(56) References Cited

U.S. PATENT DOCUMENTS

| | | | |
|---|---|---|---|
| 3,234,258 A | 2/1966 | Morris | |
| 3,418,243 A | 12/1968 | Hoxie | |
| 3,915,878 A * | 10/1975 | Yurko et al. | 510/349 |
| 4,051,054 A * | 9/1977 | Davies et al. | 510/438 |
| 4,145,184 A * | 3/1979 | Brain et al. | 8/137 |
| 4,152,272 A * | 5/1979 | Young | 510/101 |
| 4,234,627 A * | 11/1980 | Schilling | 8/137 |
| 4,238,346 A | 12/1980 | Sugahara et al. | |
| 4,446,032 A * | 5/1984 | Munteanu et al. | 510/515 |
| 4,464,271 A * | 8/1984 | Munteanu et al. | 510/515 |
| 4,524,009 A | 6/1985 | Valenty | |
| 4,639,325 A | 1/1987 | Valenty et al. | |
| 4,713,193 A * | 12/1987 | Tai | 510/532 |
| 4,816,553 A | 3/1989 | Baur et al. | |
| 4,908,233 A * | 3/1990 | Takizawa et al. | 427/213.35 |
| 4,954,285 A * | 9/1990 | Wierenga et al. | 510/101 |
| 4,973,422 A * | 11/1990 | Schmidt | 510/337 |
| 4,985,553 A | 1/1991 | Fuertes et al. | |
| 4,997,599 A * | 3/1991 | Steiner et al. | 264/5 |
| 5,075,041 A | 12/1991 | Lutz | |
| 5,223,251 A * | 6/1993 | Nichols | 424/69 |
| 5,246,603 A * | 9/1993 | Tsaur et al. | 510/519 |
| 5,384,364 A * | 1/1995 | Besse et al. | 510/231 |
| 5,453,216 A * | 9/1995 | Kellett | 510/220 |
| 5,494,488 A | 2/1996 | Arnoldi et al. | |
| 5,501,814 A | 3/1996 | Engelskirchen et al. | |
| 5,541,316 A | 7/1996 | Engelskirchen et al. | |
| 5,580,941 A | 12/1996 | Krause et al. | |
| 5,783,545 A * | 7/1998 | Paatz et al. | 510/305 |
| 5,821,360 A | 10/1998 | Engelskirchen et al. | |
| 5,830,956 A | 11/1998 | Stockhausen et al. | |
| 5,840,668 A * | 11/1998 | Behan et al. | 510/112 |
| 5,904,758 A | 5/1999 | Kucala, III | |
| 5,912,218 A * | 6/1999 | Chatterjee et al. | 510/220 |
| 5,922,670 A | 7/1999 | Knuebel et al. | |
| 5,959,101 A | 9/1999 | Engelskirchen et al. | |
| 6,024,943 A * | 2/2000 | Ness et al. | 424/59 |
| 6,042,792 A * | 3/2000 | Shefer et al. | 422/259 |
| 6,056,791 A | 5/2000 | Weidner et al. | |
| 6,075,001 A | 6/2000 | Wilde | |
| 6,103,379 A * | 8/2000 | Margel et al. | 428/403 |
| 6,187,055 B1 | 2/2001 | Kottwitz et al. | |
| 6,211,136 B1 | 4/2001 | Richter et al. | |
| 6,235,274 B1 * | 5/2001 | Lou et al. | 424/65 |
| 6,248,703 B1 * | 6/2001 | Finucane et al. | 510/152 |
| 6,303,560 B1 | 10/2001 | Hartan et al. | |
| 6,362,159 B1 * | 3/2002 | Aguadisch et al. | 512/4 |

(Continued)

FOREIGN PATENT DOCUMENTS

CA 2 053 900 10/1990

(Continued)

OTHER PUBLICATIONS

Jakobi et al., "Detergents and Textile Washing", VCH-Verlag, Weihheim, p. 94 (1987).

(Continued)

*Primary Examiner*—Lorna M Douyon
(74) *Attorney, Agent, or Firm*—David LeCroy

(57) ABSTRACT

A washing and cleaning agent shaped body in the form of a granulate, extrudate, agglomerate, or tablet, containing fine microparticles that contain one or more washing or cleaning agent components, wherein the fine microparticles form the shaped body as such or are present within it. The washing or cleaning agent component is selected from surfactants, fragrances, dyes, enzymes, enzyme stabilizers, builders, substances to adjust the pH, bleaches, bleach activators, silver protectants, soil-repelling substances, optical brighteners, antiredeposition agents, disintegration auxiliaries, and mixtures thereof. At least 10% of the fine microparticles, based on the total number of microparticles, have a particle size distribution of $\leq 20$ μm.

32 Claims, No Drawings

U.S. PATENT DOCUMENTS

| | | | | |
|---|---|---|---|---|
| 6,368,633 | B1 * | 4/2002 | Lou et al. | 424/489 |
| 6,475,982 | B1 * | 11/2002 | Beagle et al. | 510/507 |
| 6,491,902 | B2 * | 12/2002 | Shefer et al. | 424/70.1 |
| 6,562,769 | B1 | 5/2003 | Paatz et al. | |
| 6,608,017 | B1 * | 8/2003 | Dihora et al. | 510/349 |
| 6,660,704 | B1 * | 12/2003 | Waschenbach et al. | 510/298 |
| 6,849,591 | B1 * | 2/2005 | Boeckh et al. | 510/475 |
| 6,881,359 | B2 * | 4/2005 | Leeners et al. | 264/9 |
| 6,911,054 | B2 | 6/2005 | Boeckh et al. | |
| 6,951,836 | B2 * | 10/2005 | Jahns et al. | 510/441 |

FOREIGN PATENT DOCUMENTS

| | | |
|---|---|---|
| CA | 2314035 | 1/2001 |
| DE | 3511515 | 10/1985 |
| DE | 42 21 381 C1 | 2/1994 |
| DE | 43 00 772 A1 | 7/1994 |
| DE | 43 03 320 A1 | 8/1994 |
| DE | 43 21 022 A1 | 1/1995 |
| DE | 44 17 734 A1 | 11/1995 |
| DE | 44 43 177 A1 | 6/1996 |
| DE | 195 03 061 A1 | 8/1996 |
| DE | 195 13 391 A1 | 10/1996 |
| DE | 195 40 086 A1 | 4/1997 |
| DE | 196 16 767 A1 | 6/1997 |
| DE | 196 00 018 A1 | 7/1997 |
| DE | 196 16 693 A1 | 11/1997 |
| DE | 196 16 769 A1 | 11/1997 |
| DE | 196 16 770 A1 | 11/1997 |
| DE | 19635405 | 3/1998 |
| DE | 19746780 | 4/1999 |
| DE | 198 28 579 A1 | 12/1999 |
| DE | 198 55 676 A1 | 6/2000 |
| DE | 19932569 | 1/2001 |
| EP | 0 150 930 A2 | 8/1985 |
| EP | 0 232 202 A2 | 8/1987 |
| EP | 0 280 223 A2 | 8/1988 |
| EP | 0 340 989 A2 | 11/1989 |
| EP | 0376385 A2 * | 7/1990 |
| EP | 0 427 349 A2 | 5/1991 |
| EP | 0 472 042 A1 | 2/1992 |
| EP | 0 542 496 A1 | 5/1993 |
| EP | 0 703 292 A1 | 3/1996 |
| EP | 0764717 A1 * | 3/1997 |
| EP | 0 525 239 B1 | 7/1997 |
| EP | 0 744 992 B1 | 10/1997 |
| EP | 0881281 | 12/1998 |
| EP | 0 953 631 A1 | 11/1999 |
| EP | 0 987 317 A1 | 3/2000 |
| EP | 1043391 | 10/2000 |
| GB | 2066839 A * | 7/1981 |
| JP | 58-217598 | 12/1983 |
| JP | 93-339896 | 12/1993 |
| WO | WO 90/03782 A2 | 4/1990 |
| WO | WO 90/13533 A1 | 11/1990 |
| WO | WO 92/18542 A1 | 10/1992 |
| WO | WO 93/08251 A1 | 4/1993 |
| WO | WO 93/16110 A1 | 8/1993 |
| WO | WO 94/01222 A1 | 1/1994 |
| WO | WO 94/27970 A1 | 12/1994 |
| WO | WO 94/28030 A1 | 12/1994 |
| WO | WO 94/28102 A1 | 12/1994 |
| WO | WO 94/28103 A1 | 12/1994 |
| WO | WO 94/28107 A1 * | 12/1994 |
| WO | WO 95/00626 A1 | 1/1995 |
| WO | WO 95/07303 A1 | 3/1995 |
| WO | WO 95/12619 A1 | 5/1995 |
| WO | WO 95/14075 A1 | 5/1995 |
| WO | WO 95/14759 A1 | 6/1995 |
| WO | WO 95/17498 A1 | 6/1995 |
| WO | WO 95/19953 A1 | 7/1995 |
| WO | WO 95/19954 A1 | 7/1995 |
| WO | WO 95/19955 A1 | 7/1995 |
| WO | WO 95/20029 A1 | 7/1995 |
| WO | WO 95/20608 A1 | 8/1995 |
| WO | WO 97/11152 A1 * | 3/1997 |
| WO | WO 98/41607 | 9/1998 |
| WO | WO 99/10467 A1 | 3/1999 |
| WO | WO 99/44565 | 9/1999 |
| WO | WO 00/66704 | 11/2000 |
| WO | WO 01/00766 A1 | 1/2001 |
| WO | WO 01/04257 A1 * | 1/2001 |
| WO | WO 01/40430 A1 * | 6/2001 |
| WO | WO 01/94515 | 12/2001 |

OTHER PUBLICATIONS

Rompp, Tensiometer, $9^{th}$ Edition, vol. 6, p. 4440, Verlag Stuttgart, New York, 1999.

Voigt, Lehrbuch der pharmazeutischen Technologie, $6^{th}$ Edition, pp. 182-184(1987).

* cited by examiner

WASHING AND CLEANING AGENTS COMPRISING FINE MICROPARTICLES WITH CLEANING AGENT COMPONENTS

REFERENCE TO RELATED APPLICATIONS

This is a continuation application under 35 U.S.C. §365(c) of International Application No. PCT/EP02/00881, filed Jan. 29, 2002 in the European Patent Office, and claiming priority under 35 U.S.C. § 119 of DE 101 05 801.2, filed Feb. 7, 2001 in the German Patent Office.

BACKGROUND OF THE INVENTION

The present application relates to washing and cleaning agents which have fine microparticles with cleaning agent components, to the use thereof and to a process for their preparation.

Washing and cleaning agents suitable for the cleaning of hard and soft surfaces are well known in the prior art. Washing and cleaning agents which have the cleaning agent components in solid form, including, for example, powders, tablets and solutions and gels which comprise solid particles, have the disadvantage that there is the risk of gelling when such particles are dissolved.

Thus, washing and cleaning agent particles during the dispersion and dissolution process have a "corona" around the washing agent particles at the start of the dissolution phase in the aqueous medium after a dissolution time of a few minutes. This is a gel phase, often with liquid-crystalline phases, which can considerably hinder the further diffusion process and thus the dissolution rate (=gelling effect).

Thus, particularly in the case of washing agents during the dissolution of cleaning agent active substances, for example surfactants or the like, gelling arises in the dosing compartment or in the wash liquor.

The gelling of cleaning agent active substances leads to poorer dispersibility, reduced solubility, inhomogeneous distribution in the wash liquor, impaired cleaning action, and the formation of cleaning agent residues in the dosing compartment and/or on clothing.

A further disadvantage of these washing and cleaning agents known in the prior art is that the particles used customarily in washing and cleaning agents lead, as a result of their size, to significant concentration differences in the washing and cleaning agent and consequently also at the site of use, even where the inhomogeneity of the washing and cleaning agent composition is low. This can impair the cleaning performance.

In order to counteract this effect, the washing and cleaning agents often have an excessively high content of cleaning agent active substances, fragrances, dyes and the like.

Another disadvantage of the solid washing agents known in the prior art is that high proportions of nonionic surfactant lead to sticky washing agents. It is, however, specifically the nonionic surfactants which have excellent cleaning performances particularly in the case of fat-like soilings.

A high proportion of nonionic surfactants can, if the surfactants are distributed inhomogeneously and are located specifically at the particle surface, lead to inadequate ability to be stored in silos and/or to poor pourability, pumpability or flowability as a result of clumping.

A further disadvantage with solid washing and cleaning agents is that excessively large particles often have poor dissolution behavior.

Finally, in the case of solid washing agents, fragrances are usually sprayed onto the surface of the product following preparation of the powder or granulate in a downstream process step. A disadvantage of this process is that the fragrance is not incorporated by it into the powder or granulate, and thus can readily evaporate from the surface. In order to maintain an adequately perceptible scent of the washing and cleaning agent over a prolonged period of use at the site of use, the fragrance is therefore overdosed in order to counteract increased evaporation.

An object of the present invention is to overcome the disadvantages given above in the prior art.

This object is achieved according to the invention by washing and cleaning agents, where the washing and cleaning agent comprises fine microparticles, where the fine microparticles have one or more cleaning agent components.

Further advantageous embodiments are listed in the dependent claims, to which reference is made in their entirety.

DESCRIPTION OF THE INVENTION

Surprisingly, it has now been found that for fine microparticles comprising cleaning agent components, the gelling effect at the site of use upon dilution with an aqueous medium does not arise or is at least significantly reduced. For example, it has been found for surfactants, in particular for nonionic surfactants, that the gelling effect in the dosing compartment and wash liquor did not arise or arose only to a very small extent.

In addition, for washing and cleaning agents which comprise cleaning agent components in the form of fine microparticles, better dispersibility, increased dissolution rate, more homogeneous distribution and improved cleaning action in the wash liquor have been found.

In addition, encrustations, for example caused by lumps formed by means of gelling, or the like, in the dosing compartment, in feed lines and discharge lines as a result of detergent residues are prevented or at least reduced.

Without wishing to be bound to a particular theory, these effects are presumably attributable in particular to the reduced gelling effect.

A further advantage of cleaning agent components in the form of fine microparticles is that they permit a more uniform or more homogeneous distribution in washing and cleaning agents.

In addition, as a result of a uniform distribution of the cleaning agent components according to the invention in the form of fine microparticles, it is possible to achieve a higher proportion by weight, based on the washing and cleaning agent overall composition, for example for surfactants, in particular nonionic surfactants, as a result of the supporting effect of the surrounding powder matrix of the washing or the cleaning agent. The better distribution of the nonionic surfactant or of the perfume here reduces the tendency towards stickiness of the overall product. On the basis of the reduced gelling effect, the cleaning performance of the washing and cleaning agent can be increased since more washing and cleaning agent particle components enter into solution at the start of the washing process and thus actively participate in the cleaning process.

The distribution of the washing and cleaning agent components, such as surfactants, fragrances or the like, in a fine microparticle takes place advantageously by a carrier principle. In the carrier principle, the fragrance must be introduced into the fine microparticle without destroying it. Following insertion, the washing and cleaning agent component must be held firmly within the particle without separation, for example pushing to the particle surface or similar taking place during storage.

Since fragrances, such as perfume oils, are hydrophobic, relatively large perfume oil contents, e.g. in the case of scent beads for admixing in washing agent preparations, likewise lead to dispersion and solubility problems. Fine microparticles which have a fragrance or perfume content lead, as in the case of the nonionic surfactants, thus also to better dosing and dispersion behavior than coarse particles with the same ingredients.

It is important that the finely divided fragrances, such as perfume or surfactant particles etc., in the ready-to-use washing and cleaning agent composition are present in undestroyed form. If the fine microparticles are crushed and/or combined with the washing and cleaning agent residual matrix, relatively unfavorable dispersion, dissolution and storage properties arise as a result of the gel effect.

The use of finely divided fragrance and surfactant particles in washing and cleaning agent preparations, in particular of tabs, granules and/or extrudates, is particularly advantageous.

The washing and cleaning agents according to the invention can comprise at least one shaped body.

The shaped body/bodies is/are preferably compacted shaped bodies. The shaped bodies can have fine microparticles. The fine microparticles can be applied to the outer surface of the shaped body, form the shaped body as such and/or be present within the shaped body.

It is particularly preferred that the shaped bodies release microparticles at the site of use. For the purposes of this invention, site of use is the site and the time at which the washing and cleaning agent components are released for the purpose of cleaning or soil removal and/or the washing and cleaning agents become active for the purpose of cleaning or soil removal. The microparticles are preferably released at the start of the washing/cleaning process, but can also be released at an earlier or later time. The purpose of release can also be fabric conditioning or perfuming.

The degree of compaction of the shaped bodies is preferably chosen so that the shaped body releases fine microparticles at the site of use. The microparticles have a larger ratio of surface area to volume than coarse particles and distribute themselves better in the solution medium. In this way, in the case of washing agents according to the invention, when the shaped bodies dissolve in the wash liquor, the gelling effect is counteracted by the release of fine microparticles.

Suitable shaped bodies include, inter alia, granulates, extrudates, particles, agglomerates, capsules, tablets, tabs and/or the like, and mixtures thereof.

These shaped bodies can also be used in a surrounding liquid washing agent or cleaner vicinity.

In addition, the fine microparticles can be present in the washing and cleaning agent in compacted and/or noncompacted form.

It is particularly preferred according to the invention that the fine microparticles in the washing and cleaning agent composition are present in at least partially undestroyed form, preferably in undestroyed form.

In the compacted form, the fine microparticles can as such form shaped bodies such as particles, agglomerates, tablets, such as tabs and/or the like, and mixtures thereof.

Preference is given to those particles, agglomerates, tablets, such as tabs and/or the like, and also mixtures thereof, which release the fine microparticles again at the site of use, for example in the wash liquor. The fine microparticles can, however, also be compacted with other washing agent components to give agglomerates. Preference is given in particular to so-called Megaperls, obtainable from Henkel KGaA.

Preference is given to those Megaperls which release the fine microparticles again at the site of use, for example in the wash liquor.

It is particularly advantageous that, by using the fine microparticles, washing and cleaning agglomerates can be formed, such as, for example, Megaperls, in which, by means of admixing fine microparticles, a finely divided, i.e. very good volume distribution of the fine microparticles, and simultaneously good homogeneous distribution can be achieved.

It has been found with the washing and cleaning agent according to the invention that particularly in the case of washing agents, granulates, extrudates and washing and cleaning agent tablets, by using fine microparticles having fragrances, some of the fragrance loses its scent as soon as the package is opened, resulting in a good scent impression for the consumer, due to the fine microparticles comprising fragrances, but an adequate amount of fragrance remains in the washing and cleaning agent for the good scent impression to be retained over an extended consumption period, in particular until the washing and cleaning agent is used up. Furthermore, sufficient amounts of fragrance can in this way likewise be released in the wash liquor.

The fragrance content in washing and cleaning agents, in particular in washing agent solid bodies, is very low. The content is usually 0.5% by weight, based on the total composition of the washing and cleaning agent. In order to ensure a homogeneous distribution of the fragrances, a very finely divided distribution, which can be ensured by the fine microparticles, is very advantageous. This applies both for the washing and cleaning agent as such, for example washing agent powder, and also for washing and cleaning agent agglomerates or washing agent particles such as Megaperls, in which a uniform, finely divided distribution is desirable.

Conventional Megaperls have a diameter of 1.4 mm and weigh 0.1 g, i.e. in the case of uniform fragrance distribution over all Megaperls and 0.5% of fragrance, an amount of 0.5 mg of fragrance results. Being the only drop, this is a drop with a diameter of about 200 µm. In order to achieve as optimal, uniform distribution of the fragrance within the Megaperl and at the surface thereof as possible, fine microparticles $\leq 20$ µm are particularly advantageous.

For the purposes of the invention, the term "fine microparticles" includes inter alia also very small particles, such as nanoparticles.

The particle size of the fine microparticles are $\leq 100$ µm, preferably $\leq 50$ µm and further preferably $\leq 20$ µm. The particle sizes of the fine microparticles can, however, also be $\leq 10$ µm, preferably $\leq 5$ µm, further preferably $\leq 2$ µm, $\leq 1$ µm, $\leq 0.5$ µm, $\leq 0.1$ µm, $\leq 0.05$ µm and even $\leq 0.01$ µm.

Suitable particle sizes of the fine microparticles are $x_{90}=80$ µm and particularly preferably $x_{90}=5$ µm.

In a preferred embodiment of the invention, the fine microparticles of the washing and cleaning agent have a particle size from between 0.001 µm to 50 µm, preferably from between 0.01 to 20 µm, more preferably from between 0.05 to 10 µm, further preferably from between 0.1 to 5 µm, and most preferably between 0.5 µm to 1 µm.

In a further preferred embodiment of the invention, $\geq 10\%$, preferably $\geq 30\%$, more preferably $\geq 50\%$, further preferably $\geq 70\%$, even more preferably $\geq 80\%$, and most preferably $\geq 90\%$, of the fine microparticles, based on the total number of fine microparticles, have a particle size distribution of $\leq 20$ µm.

It is particularly advantageous if the fine microparticles are subjected to a mechanical compaction process.

For example, the washing and cleaning agent can have fine microparticles which have been subjected to a mechanical compaction process, where these fine microparticles are released in undestroyed form in the washing and/or cleaning process.

In addition, the washing and cleaning agent can have shaped bodies which have been subjected to a mechanical compaction process, where the shaped bodies have undestroyed microparticles.

In a preferred embodiment, the washing and cleaning agents have fine microparticles which have been subjected to a mechanical compaction process, where ≧10%, preferably ≧30%, more preferably ≧50%, further preferably ≧70%, even more preferably ≧80%, and most preferably ≧90%, of the fine microparticles, based on the total number of the fine microparticles of the washing and cleaning agent, are released at the start of the dissolution phase in the washing and/or cleaning liquor.

In a further preferred embodiment, the washing and cleaning agents have microparticles which have been subjected to a mechanical compaction process, where ≧10%, preferably ≧30%, more preferably ≧50%, further preferably ≧70%, even more preferably ≧80%, and most preferably ≧90%, of the fine microparticles, based on the total number of the fine microparticles of the washing and cleaning agent, are released at the start of the dissolution phase with a particle size distribution of ≦50 μm into the washing and/or cleaning liquor.

The fine microparticles can be subjected to a compaction process. The compaction of the fine microparticles is preferably chosen so that during release of the fine microparticles in the washing and/or cleaning liquor, they are released undestroyed or partially undestroyed. The wording "undestroyed" means that the fine microparticles are released with a particle size distribution of ≦50 μm into the washing and/or cleaning liquor.

According to the invention, the fine microparticles have washing and cleaning agent components which may be absorbed, adsorbed and/or embedded in coating substances on carrier materials.

The carrier materials and/or coating substances can be chosen from the group consisting of salts, such as sulfates, carbonates, phosphates, acetates; organic and inorganic acids, such as citric acid, tartaric acid, malic acid, alginic acid, glutamic acid; sugars, such as sucrose, glucose, fructose, sorbitol, lactose; starch and cellulose compounds, such as potato starch, corn starch, rice starch, manioc starch, carob seed grain, cyclodextrins, algin, gelatins; further natural and synthetic polymers, such as polyvinylpyrrolidone (PVP), polyacrylic acid, polyacrylates, maleic acid-acrylic acid copolymers, PEG; silicates, such as waterglass, zeolites, metasilicates, soda silicates; silicas; surfactants, such as alkylbenzenesulfonates, fatty alcohol sulfate, stearates and/or urea.

The fine microparticles in combination with carriers and/or coating substances form shaped bodies.

The washing and cleaning agent components can be present as a gel, in solid and/or liquid form in the fine microparticles according to the invention.

The washing and cleaning agent components of the fine microparticles are preferably chosen from the group consisting of surfactants, fragrances, dyes, enzymes, enzyme stabilizers, builders, substances for adjusting the pH, bleaches, bleach activators, silver protectants, soil-repelling substances, optical brighteners, antiredeposition agents, disintegration auxiliaries, customary ingredients and/or mixtures thereof.

The washing and cleaning agent usually comprises the fine microparticles with a content of between >0% by weight and 100% by weight, preferably from between 0.01% by weight and 90% by weight, more preferably from between 0.1% by weight and 70% by weight, further preferably from between 1% by weight and 60% by weight, even more preferably from between 10% by weight and 50% by weight and most preferably from between 20% by weight and 40% by weight, based on the total composition of the washing and cleaning agent having fine microparticles.

The washing and cleaning agent particularly preferably comprises the fine microparticles with a content of between >0.05% by weight and 15% by weight, preferably from between 0.1% by weight and 10% by weight, more preferably from between 0.2% by weight and 5% by weight, further preferably from between 0.3% by weight and 3% by weight, even more preferably from between 0.4% by weight and 2% by weight, and most preferably from between 0.5% by weight and 1% by weight, based on the total composition of the washing and cleaning agent having fine microparticles.

It is advantageous that the microparticle has a content of at least one washing and cleaning agent component of between >0% by weight and 100% by weight, preferably from between 1% by weight and 90% by weight, more preferably from between 5% by weight and 70% by weight, further preferably from between 10% by weight and 60% by weight, even more preferably from between 20% by weight and 50% by weight, and most preferably between 30% by weight and 40% by weight, based on the total composition of the fine microparticle.

It is particularly preferred if the washing and cleaning agent has fine microparticles, where the microparticles have an identical or different composition of washing and cleaning agent components.

The washing and cleaning agents according to the invention comprising fine microparticles can be in solid or liquid form. Preferably, the washing and cleaning agent has two or more phases. The washing and cleaning agent is even more preferably a temporary emulsion.

The washing and cleaning agent according to the invention can be used for the cleaning of hard surfaces and/or soft surfaces.

The washing and cleaning agents can be used, in particular, as dishwashing detergents, all-purpose cleaners, bath cleaners, floor cleaners, automobile cleaners, glass cleaners, furniture care compositions or cleaners, facade cleaners, washing agents and/or the like.

In addition, the washing and cleaning agent is suitable for cleaning hair, fibers, textiles, carpets, items of clothing, foods and/or the like.

Unless stated otherwise, weight data refers to the total composition of the washing and cleaning agent having fine microparticles.

The term cleaning agent component for the purposes of this invention stands for cleaning agent components and washing agent components, unless stated otherwise.

According to the invention, all washing and cleaning agents known in the prior art can be used provided these can comprise fine microparticles.

It goes without saying that the fine microparticles have the cleaning components used for the preparation of the microparticles.

The fine microparticles can have one and/or more washing and cleaning agent components. Preferably, the fine microparticles have an active content of one or more washing and/or cleaning agent components.

The washing and cleaning agents can have mixtures of fine microparticles which are identical or different in terms of their composition with one and/or more washing and cleaning agent components.

It is particularly preferred if the fine microparticles are homogeneously distributed in the washing and cleaning agent.

The suitable washing and cleaning agent components are explained individually in more detail below.

Builders

The fine microparticles according to the invention of the washing and cleaning agents can comprise, as builders, all builders customarily used in washing and cleaning agents, in particular in washing agents, in particular therefore zeolites, silicates, carbonates, organic cobuilders and also the phosphates.

Suitable crystalline, layered sodium silicates have the general formula $NaMSi_xO_{2x+1}.H_2O$, where M is sodium or hydrogen, x is a number from 1.9 to 4 and y is a number from 0 to 20 and preferred values for x are 2, 3 or 4. Preferred crystalline phyllosilicates of the given formula are those in which M is sodium and x assumes the values 2 or 3. In particular, both β- and δ-sodium disilicates $Na_2Si_2O_5.yH_2O$ are preferred.

It is also possible to use amorphous sodium silicates with $Na_2O:SiO_2$ modulus of from 1:2 to 1:3.3, preferably from 1:2 to 1:2.8 and in particular from 1:2 to 1:2.6. Particular preference is given to amorphous silicates.

A finely crystalline, synthetic zeolite containing bonded water which can be used is preferably zeolite A and/or P. As zeolite P, particular preference is given to Zeolite MAP® (commercial product from Crosfield). Also suitable, however, are zeolite X and mixtures of A, X and/or P. A product which is commercially available and can preferably be used for the purposes of the present invention is, for example, also a cocrystallizate of zeolite X and zeolite A (about 80% by weight of zeolite X), which is sold by CONDEA Augusta S.p.A. under the trade name VEGOBOND AX® and by the formula

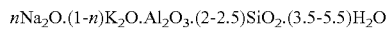

$nNa_2O.(1-n)K_2O.Al_2O_3.(2-2.5)SiO_2.(3.5-5.5)H_2O$

Suitable zeolites have an average particle size of less than 10 μm (volume distribution; measurement method: Coulter Counter) and preferably comprise 18 to 22% by weight, in particular 20 to 22% by weight, of bonded water.

It is of course also possible to use the generally known phosphates as builder substances provided such a use is not to be avoided for ecological reasons. In particular, the sodium salts of orthophosphates, of pyrophosphates and in particular of tripolyphosphates are suitable.

As organic cobuilders, in particular polycarboxylates/polycarboxylic acids, polymeric polycarboxylates, aspartic acid, polyacetals, dextrins, further organic cobuilders (see below) and phosphonates may be present in the fine microparticles according to the invention of the washing and cleaning agents. These classes of substances are described below.

Organic builder substances which can be used are, for example, the polycarboxylic acids which can be used in the form of their sodium salts, polycarboxylic acids being understood as meaning those carboxylic acids which carry more than one acid function. For example, these are citric acid, adipic acid, succinic acid, glutaric acid, malic acid, tartaric acid, maleic acid, fumaric acid, sugar acids, aminocarboxylic acids, nitrilotriacetic acid (NTA), if such a use is not objectionable for ecological reasons, and mixtures of these. Preferred salts are the salts of the polycarboxylic acids, such as citric acid, adipic acid, succinic acid, glutaric acid, tartaric acid, sugar acids and mixtures of these.

The acids per se can also be used. As well as their builder action, the acids typically also have the property of an acidifying component and thus also serve to set a relatively low and relatively mild pH of washing and/or cleaning agents. In particular, mention is made here of citric acid, succinic acid, glutaric acid, adipic acid, gluconic acid and any mixtures of these.

Suitable builders are also polymeric polycarboxylates, these are, for example, the alkali metal salts of polyacrylic acid or of polymethacrylic acid, for example those with a relative molecular mass of from 500 to 70 000 g/mol.

For the purposes of the specification, the molar masses given for polymeric polycarboxylates are weight-average molar masses $M_w$ of the respective acid form, which have been determined in principle by means of gel permeation chromatography (GPC), using a UV detector. The measurement was made here against an external polyacrylic acid standard which due to its structural similarity to the polymers under investigation, produced realistic molecular weight values. These data differ significantly from the molecular weight data for which polystyrene sulfonic acids are used as standard.

The molar masses measured against polystyrenesulfonic acids are usually considerably higher than the molar masses given in this specification.

Suitable polymers are in particular polyacrylates which preferably have a molecular mass of from 2 000 to 20 000 g/mol. From this group, due to their superior solubility, the short-chain polyacrylates, which have molar masses of from 2 000 to 10 000 g/mol, and particularly preferably from 3 000 to 5 000 g/mol, may in turn be preferred.

Also suitable are copolymeric polycarboxylates, in particular those of acrylic acid with methacrylic acid and of acrylic acid or methacrylic acid with maleic acid. Copolymers of acrylic acid with maleic acid which comprise 50 to 90% by weight of acrylic acid and 50 to 10% by weight of maleic acid have proven particularly suitable. Their relative molecular mass, based on free acids, is generally 2 000 to 70 000 g/mol, preferably 20 000 to 50 000 g/mol and in particular 30 000 to 40 000 g/mol.

The content of (co-)polymeric polycarboxylates in the fine microparticles of the washing and cleaning agent is preferably 0.5 to 20% by weight, in particular 3 to 10% by weight.

To improve the solubility in water, the fine microparticles can also comprise allylsulfonic acids, such as, for example, allyloxybenzenesulfonic acid and methallylsulfonic acid, as monomer.

Particular preference is also given to biodegradable polymers of more than two different monomer units, for example those which comprise, as monomers, salts of acrylic acid and of maleic acid, and also vinyl alcohol or vinyl alcohol derivatives or which comprise, as monomers, salts of acrylic acid and of 2-alkylallylsulfonic acid and also sugar derivatives.

Further preferred copolymers are those which have, as monomers, preferably acrolein and acrylic acid/acrylic acid salts or acrolein and vinyl acetate.

Further preferred builder substances which may likewise be mentioned are polymeric aminodicarboxylic acids, salts thereof or precursor substances thereof. Particular preference is given to polyaspartic acids or salts and derivatives thereof which, as well cobuilder properties, also have a bleach-stabilizing effect.

Further suitable builder substances are polyacetals, which can be obtained by reacting dialdehydes with polyolcarboxylic acids which have 5 to 7 carbon atoms and at least 3 hydroxyl groups. Preferred polyacetals are obtained from dialdehydes such as glyoxal, glutaraldehyde, terephthalaldehyde and mixtures thereof and from polyolcarboxylic acids, such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary, for example acid- or enzyme-catalyzed, processes. They are preferably hydrolysis products with average molar masses in the range from 400 to 500 000 g/mol. In this connection, a polysaccharide with a dextrose equivalent (DE) in the range from 0.5 to 40, in particular from 2 to 30, is preferred, where DE is a customary measure of the reducing effect of a polysaccharide compared with dextrose, which has a DE of 100. It is possible to use both maltodextrins with a DE between 3 and 20 and dry glucose syrups with a DE between 20 and 37, and also so-called yellow dextrins and white dextrins with higher molar masses in the range from 2 000 to 30 000 g/mol.

The oxidized derivatives of such dextrins are their reaction products with oxidizing agents which are able to oxidize at least one alcohol function on their saccharide ring to the carboxylic acid function. A product oxidized on $C_6$ of the saccharide ring may be particularly advantageous.

A preferred dextrin is described in British patent application 94 19 091. The oxidized derivatives of such dextrins are their reaction products with oxidizing agents which are able to oxidize at least one alcohol function on the saccharide ring to the carboxylic acid function. Such oxidized dextrins and processes for their preparation are known, for example, from European patent applications EP-A-0 232 202, EP-A-0 427 349, EP-A-0 472 042 and EP-A-0 542 496, and the International patent applications WO-A-92/18542, WO-A-93/08251, WO-A-94/28030, WO-A-95/07303, WO-A-95/12619 and WO-A-95/20608. A product oxidized on C6 of the saccharide ring may be particularly advantageous.

Oxydisuccinates and other derivatives of disuccinates, preferably ethylenediamine disuccinate, are also further suitable cobuilders. In this connection, ethylenediamine N,N'-disuccinate (EDDS) is preferably used in the form of its sodium or magnesium salts. In addition, preference is given in this connection also to glycerol disuccinates and glycerol trisuccinates, as are described, for example, in US-American patent specifications U.S. Pat. No. 4,524,009, U.S. Pat. No. 4,639,325, in European patent application EP-A-0 150 930 and the Japanese patent application JP 93/339896.

Further organic cobuilders which can be used are, for example, acetylated hydroxycarboxylic acids and salts thereof, which can optionally also be in the lactone form and which comprise at least 4 carbon atoms and at least one hydroxyl group and at most two acid groups. Such cobuilders are described, for example, in International patent application WO-A-95/20029.

A further class of substance with cobuilder properties is represented by the phosphonates. These are, in particular, hydroxyalkanephosphonates and aminoalkane-phosphonates. Among the hydroxyalkanephosphonates, 1-hydroxyethane-1,1-diphosphonate (HEDP) is of particular importance as cobuilder. It is preferably used as the sodium salt, the disodium salt giving a neutral reaction and the tetrasodium salt giving an alkaline (pH 9) reaction. Suitable aminoalkanephosphonates are preferably ethylenediaminetetra-methylenephosphonate (EDTMP), diethylenetriamine-pentamethylenephosphonate (DTPMP) and higher homologs thereof. They are preferably used in the form of the neutrally reacting sodium salts, e.g. as the hexasodium salt of EDTMP or as the hepta- and octasodium salt of DTPMP. As a builder in this case, preference is given to using HEDP from the class of phosphonates. Furthermore, the aminoalkanephosphonates have a marked heavy-metal-binding capacity. Accordingly, and especially if the washing and cleaning agents also comprise bleach, it may be preferred to use aminoalkanephosphonates, in particular DTPMP, in the fine microparticles, or to use mixtures of said phosphonates for the preparation of the fine microparticles.

Moreover, all compounds which are able to form complexes with alkaline earth metal ions may be used as cobuilders.

Suitable polymeric polycarboxylates for the preparation of the fine microparticles are, for example, the sodium salts of polyacrylic acid or of polymethacrylic acid, for example those with a relative molecular mass of from 800 to 150 000 (based on acid). Suitable copolymeric polycarboxylates are, in particular, those of acrylic acid with methacrylic acid and of acrylic acid or methacrylic acid with maleic acid. Copolymers of acrylic acid with maleic acid which comprise 50 to 90% by weight of acrylic acid and 50 to 10% by weight of maleic acid have proven particularly suitable. Their relative molecular mass, based on free acids, is generally 5 000 to 200 000, preferably 10 000 to 120 000 and in particular 50 000 to 100 000.

The content of (co-)polymeric polycarboxylates in the washing and/or cleaning agents comprising fine microparticles is in the customary framework and is preferably 1 to 10% by weight, based on the total composition of the washing and cleaning agent.

For the preparation of the fine microparticles, particular preference is also given to biodegradable polymers of more than two different monomer units, for example those which, according to DE-A-43 00 772, comprise salts of acrylic acid and of maleic acid and also vinyl alcohol or vinyl alcohol derivatives as monomers or, according to DE-C-42 21 381, comprise salts of acrylic acid and of 2-alkylalylsulfonic acid and also sugar derivatives as monomers.

Further preferred copolymers for the preparation of the fine microparticles are those described in the German patent applications DE-A-43 03 320 and DE-A-44 17 734 and having, as monomers, preferably acrolein and acrylic acid/acrylic acid salts or acrolein and vinyl acetate.

Further suitable builder substances for the preparation of the fine microparticles are oxidation products of carboxyl-group-containing polyglucosans and/or water-soluble salts thereof, as are described, for example, in International patent application WO-A-93/08251 or the preparation of which is described, for example in International patent application WO-A-93/16110. Likewise suitable are oxidized oligosaccharides according to German patent application DE-A-196 00 018.

For the preparation of the fine microparticles, as further preferred builder substances, mention may likewise be made of polymeric aminodicarboxylic acids, salts thereof or precursor substances thereof. Particular preference is given to polyaspartic acids or salts and derivatives thereof, about which it is disclosed in German patent application DE-A-195 40 086 that, as well as cobuilder properties, they also have a bleach-stabilizing effect.

Further builder substances suitable for the preparation of the fine microparticles are polyacetals, which can be obtained by reacting dialdehydes with polyolcarboxylic acids which have 5 to 7 carbon atoms and at least 3 hydroxyl groups, for example as described in European patent application EP-A-0 280 223. Preferred polyacetals are obtained from dialdehydes such as glyoxal, glutaraldehyde, terephthalaldehyde and mixtures thereof and from polyolcarboxylic acids, such as gluconic acid and/or glucoheptonic acid.

In addition, the fine microparticles can also comprise components which have a positive influence on the ability to wash oil and grease out of textiles. This effect is particularly important when a textile is soiled which has already been washed beforehand a number of times with a washing agent according to the invention which comprises this oil- and grease-release component. Preferred oil- and grease-releasing components include, for example, nonionic cellulose ethers, such as methylcellulose and methylhydroxy-propylcellulose with a proportion of methoxyl groups of from 15 to 30% by weight and of hydroxypropoxyl groups of from 1 to 15% by weight, in each case based on the nonionic cellulose ethers, and the polymers of phthalic acid and/or of terephthalic acid known from the prior art, or of derivatives thereof, in particular polymers of ethylene terephthalates and/or polyethylene glycol terephthalates or anionically and/or nonionically modified derivatives of these. Of these, particular preference is given to the sulfonated derivatives of phthalic acid and of terephthalic acid polymers.

Ingredients

Further suitable ingredients of the fine microparticles are water-soluble inorganic salts, such as bicarbonates, carbonates, amphous silicates, such as the above-mentioned dissolution-delayed silicates or mixtures of these; in particular, alkali metal carbonate and amorphous alkali metal silicate, primarily sodium silicate with an Na2O:SiO2 molar ratio of from 1:1 to 1:4.5, preferably from 1:2 to 1:3.5, are used. The content of sodium carbonate in the washing and cleaning agents comprising fine microparticles is here preferably up to 20% by weight, advantageously between 5 and 15% by weight, based on the total composition of the washing and cleaning agent. The content of sodium silicate in the washing and cleaning agents comprising fine microparticles is—if it is not intended to be used as a builder substance, generally up to 10% by weight and preferably between 2 and 8% by weight, otherwise above this, based on the total composition of the washing and cleaning agent.

According to the teaching of International patent application WO-A-94/01222, alkali metal carbonates can also be replaced by sulfur-free amino acids having 2 to 11 carbon atoms and optionally a further carboxyl and/or amino group, and/or by salts thereof. For the purposes of this invention, it is possible for some or all of the alkali metal carbonates to be replaced by glycine or glycinate.

Other components

The other components of the fine microparticles which can be used, include, for example, antiredeposition agents (soil carriers), foam inhibitors, bleaches and bleach activators, optical brighteners, enzymes, textile-softening substances, color and scent, and also neutral salts such as sulfates and chlorides in the form of their sodium or potassium salts.

Agents to Adjust the pH

To reduce the pH of washing and cleaning agents, in particular washing agents, the fine microparticles can also have acidic salts or slightly alkaline salts. Preferred acidification components here are bisulfates and/or bicarbonates or the above-mentioned organic polycarboxylic acids, which can simultaneously also be used as builder substances. Particular preference is given to the use of citric acid.

Surfactants

Surfactants which can be used for the preparation of the fine microparticles are preferably anionic, cationic, amphoteric and/or nonionic surfactants, preference being given to anionic surfactants and nonionic surfactants. Important ingredients of the agents according to the invention and ingredients which are used in the process according to the invention are surfactants, in particular anionic surfactants, which should be present at least in amounts of 0.5% by weight in the washing and cleaning agents comprising fine particles and in accordance with the invention, or washing and cleaning agents comprising fine microparticles prepared according to the invention. These include, in particular, sulfonates and sulfates, but also soaps.

Anionic Surfactants

The anionic surfactants used are, for example, those of the sulfonate and sulfate type. Suitable surfactants of the sulfonate type are, preferably $C_9$-$C_{13}$-alkylbenzenesulfonates, olefinsulfonates, i.e. mixtures of alkene- and hydroxyalkanesulfonates, and disulfonates, as are obtained, for example, from $C_{12-18}$-monoolefins having a terminal or internal double bond by sulfonation with gaseous sulfur trioxide and subsequent alkaline or acidic hydrolysis of the sulfonation products. Also suitable are alkanesulfonates, which are obtained from $C_{12-18}$-alkanes, for example by sulfochlorination or sulfoxidation with subsequent hydrolysis or neutralization, respectively. Likewise suitable are also the esters of α-sulfo fatty acids (ester sulfonates), e.g. the α-sulfonated methyl esters of hydrogenated coconut, palm kernel or tallow fatty acids. Also suitable are sulfonation products of unsaturated fatty acids, for example oleic acid, in small amounts, preferably in amounts not exceeding about 2 to 3% by weight.

Particular preference is given to α-sulfo fatty acid alkyl esters which have an alkyl chain with not more than 4 carbon atoms in the ester group, for example methyl ester, ethyl ester, propyl ester and butyl ester. With particular advantage, the methyl esters of the α-sulfo fatty acids (MES), but also hydrolyzed disalts thereof are used particularly advantageously.

Further suitable anionic surfactants are sulfated fatty acid glycerol esters. Fatty acid glycerol esters are understood as meaning the monoesters, diesters and triesters, and mixtures thereof, as are obtained in the preparation by esterification of a monoglycerol with 1 to 3 mol of fatty acid or in the transesterification of triglycerides with 0.3 to 2 mol of glycerol. Preferred sulfated fatty acid glycerol esters here are the sulfonation products of saturated fatty acids having 6 to 22 carbon atoms, for example those of caproic acid, caprylic acid, capric acid, myristic acid, lauric acid, palmitic acid, stearic acid or behenic acid.

Preferred alk(en)yl sulfates are the alkali metal salts, and in particular the sodium salts, of the sulfuric monoesters of $C_{12}$-$C_{18}$-fatty alcohols, for example those with coconut fatty alcohol, tallow fatty alcohol, lauryl, myristyl, cetyl or stearyl alcohol or of $C_{10}$-$C_{20}$-oxo alcohols, and those monoesters of secondary alcohols of these chain lengths. Preference is also given to alk(en)yl sulfates of said chain length which contain a synthetic straight-chain alkyl radical prepared on a petrochemical basis, and which have a degradation behavior analogous to that of the corresponding compounds based on fatty-chemical raw materials. From a washing technology viewpoint, the $C_{12}$-$C_{16}$-alkyl sulfates and $C_{12}$-$C_{15}$-alkyl sulfates and also $C_{14}$-$C_{15}$-alkyl sulfates, are preferred. In addition, 2,3-alkyl sulfates, which are prepared, for example, according to US patent specifications U.S. Pat. Nos. 3,234,258 or 5,075,041 and can be obtained as commercial products from Shell Oil Company under the name DAN®, are suitable anionic surfactants.

Also suitable are the sulfuric monoesters of the straight-chain or branched $C_{7-21}$-alcohols ethoxylated with 1 to 6 mol of ethylene oxide, such as 2-methyl-branched $C_{9-11}$-alcohols containing, on average, 3.5 mol of ethylene oxide (EO) or $C_{12-18}$-fatty alcohols having 1 to 4 EO. Due to their high foaming behavior, the washing and cleaning agents according to the invention comprise the abovementioned sulfuric monoester derivatives only in relatively small amounts, for example in amounts of from 1 to 5% by weight.

Further suitable anionic surfactants for the preparation of the fine microparticles are also the salts of the alkylsulfosuccinic acid, which are also referred to as sulfosuccinates or as sulfosuccinic esters and which represent the monoesters and/or diesters of sulfosuccinic acid with alcohols, preferably fatty alcohols and in particular ethoxylated fatty alcohols. Preferred sulfosuccinates comprise $C_{8-18}$-fatty alcohol radicals or mixtures of these. Particularly preferred sulfosuccinates comprise a fatty alcohol radical derived from ethoxylated fatty alcohols, which themselves represent nonionic surfactants (for description see below). Here, particular preference is in turn given to sulfosuccinates whose fatty alcohol radicals are derived from ethoxylated fatty alcohols having a narrowed homolog distribution. It is likewise also possible to use alk(en)ylsuccinic acid with preferably 8 to 18 carbon atoms in the alk(en)yl chain or salts thereof.

Further suitable anionic surfactants are fatty acid derivatives of amino acids, for example of N-methyltaurine (taurides) and/or of N-methylglycine (sarcosides). Particular preference is given here to the sarcosides and the sarcosinates and here primarily sarcosinates of higher and optionally mono- or polyunsaturated fatty acids, such as oleyl sarcosinate.

Further suitable anionic surfactants are, in particular soaps. Suitable soaps include saturated fatty acid soaps, such as the salts of lauric acid, myristic acid, palmitic acid, stearic acid, hydrogenated erucic acid and behenic acid, and in particular mixtures of soaps derived from natural fatty acids, e.g. coconut, palm kernel or tallow fatty acids.

The anionic surfactants, including the soaps, may be present in the form of their sodium, potassium or ammonium salts and also as soluble salts of organic bases, such as mono-, di- or triethanolamine, in the fine microparticles. Preferably, the anionic surfactants are in the form of their sodium or potassium salts, in particular in the form of the sodium salts.

When selecting the anionic surfactants which are used in the fine microparticles according to the invention of the washing and cleaning agents, no restrictive conditions stand in the way of the freedom of formulation. Preferred washing and cleaning agents, however, have a content of soap which exceeds 0.2% by weight, based on the total weight of the washing and cleaning agent. Preferred anionic surfactants used here are the alkylbenzenesulfonates and fatty alcohol sulfates, where preferred washing and cleaning agents comprise 2 to 20% by weight, preferably 2.5 to 15% by weight and in particular 5 to 10% by weight, of fatty alcohol sulfate(s), in each case based on the washing and cleaning agent weight.

The anionic surfactants are present in the fine particles according to the invention preferably in amounts of from 1 to 100% by weight, preferably from 1 to 30% by weight and in particular in amounts of from 5 to 25% by weight.

As well as the anionic surfactants and the cationic, zwitterionic and amphoteric surfactants, preference is primarily given to nonionic surfactants.

Nonionic Surfactants

The nonionic surfactants used for the preparation of the fine microparticles are preferably alkoxylated, advantageously ethoxylated, in particular primary, alcohols having preferably 8 to 18 carbon atoms and, on average, 1 to 12 mol of ethylene oxide (EO) per mole of alcohol, in which the alcohol radical may be linear or, preferably, methyl-branched in position 2 and/or may comprise linear and methyl-branched radicals in a mixture, as are customarily present in oxo alcohol radicals. In particular, however, preference is given to alcohol ethoxylates with linear radicals of alcohols of natural origin having 12 to 18 carbon atoms, e.g. from coconut, palm, tallow fatty or oleyl alcohol, and on average from 2 to 8 EO per mole of alcohol. Preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-18}$-alcohols having 3 EO, 5 EO or 7 EO and mixtures of these, such as mixtures of $C_{12-14}$-alchol having 3 EO and $C_{12-18}$-alcohol having 5 EO. The given degrees of ethoxylation are statistical average values which, for a specific product, may be an integer or a fraction. Preferred alcohol ethoxylates have a narrowed homolog distribution (narrow range ethoxylates, NREs). In addition to these nonionic surfactants, it is also possible to use fatty alcohols having more than 12 EO for the preparation of the fine microparticles. Examples thereof are tallow fatty alcohol having 14 EO, 25 EO, 30 EO or 40 EO.

A further class of preferred nonionic surfactants for the preparation of the fine microparticles, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters, as are described, for example in Japanese patent application JP 58/217598 or which are preferably prepared by the process described in International patent application WO-A-90/13533. Preferred nonionic surfactants are $C_{12}$-$C_{18}$-fatty acid methyl esters having, on average, 3 to 15 EO, in particular having, on average, 5 to 12 EO, while primarily higher ethoxylated fatty acid methyl esters are advantageous as binding agents, as described above. In particular, $C_{12}$-$C_{18}$-fatty acid methyl esters with 10 to 12 EO can be used as surfactants.

A further class of nonionic surfactants which can be used advantageously for the preparation of the fine microparticles are the alkyl polyglycosides (APGs). Alkyl polyglycosides which can be used satisfy the general formula $RO(G)_z$, in which R is a linear or branched, in particular methyl-branched in position 2, saturated or unsaturated, aliphatic radical having 8 to 22, preferably 12 to 18 carbon atoms and G is the symbol representing a glycose unit having 5 or 6 carbon atoms, preferably glucose. The degree of glycosylation z here is between 1.0 and 4.0, preferably between 1.0 and 2.0 and in particular between 1.1 and 1.4.

For the preparation of the fine microparticles, preference is given to using linear alkyl polyglucosides, i.e. alkyl polyglycosides, in which the polyglycosyl radical is a glucose radical and the alkyl radical is an n-alkyl radical.

The fine microparticles according to the invention can preferably comprise alkyl polyglycosides, preference being given to contents of APGs in the washing and cleaning agents of more than 0.2% by weight, based on the total washing and cleaning agent. Particularly preferred washing and cleaning agents containing fine microparticles have APGs in amounts of from 0.2 to 10% by weight, preferably 0.2 to 5% by weight and in particular from 0.5 to 3% by weight.

Nonionic surfactants of the amine oxide type, for example N-cocoalkyl-N,N-dimethylamine oxide and N-tallow-alkyl-N,N-dihydroxyethylamine oxide, and of the fatty acid alkanolamide type may also be suitable for the preparation of the fine microparticles. The amount of these nonionic surfactants is preferably not more than that of the ethoxylated fatty alcohols, in particular not more than half thereof.

Suitable further surfactants for the preparation of the fine microparticles are so-called gemini surfactants. These are generally understood as meaning those compounds which have two hydrophilic groups and two hydrophobic groups per molecule. These groups are generally separated from one another by a so-called "spacer". This spacer is usually a carbon chain which should be long enough for the hydrophilic groups to have a sufficient distance such that they can act independently of one another. Such surfactants are generally characterized by an unusually low critical micelle concentration and the ability to drastically reduce the surface tension of water. However, in exceptional cases, the expression "gemini surfactants" is understood as meaning not only dimeric, but also trimeric, surfactants.

Suitable gemini surfactants for the preparation of the fine microparticles are, for example, sulfated hydroxy mixed ethers according to German patent application DE-A-43 21 022 or dimer alcohol bis- and trimer alcohol tris-sulfates and ether sulfates according to German patent application DE-A-195 03 061. Terminally capped dimeric and trimeric mixed ethers according to German patent application DE-A-195 13 391 are characterized in particular by their by- and multifunctionality. Thus, said terminally capped surfactants have good wetting properties and are low-foam, meaning that they are suitable in particular for use in machine washing or cleaning processes.

However, for the preparation of the fine microparticles, it is also possible to use gemini polyhydroxy fatty acid amides or poly-polyhydroxy fatty acid amides, as are described in International patent applications WO-A-95/19953, WO-A-95/19954 and WO95-19955.

Further suitable surfactants for the preparation of the fine microparticles are polyhydroxy fatty acid amides of the formula (I),

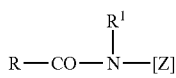

(I)

in which RCO is an aliphatic acyl radical having 6 to 22 carbon atoms, $R^1$ is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (II),

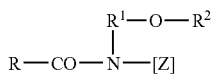

(II)

in which R is a linear or branched alkyl or alkenyl radical having 7 to 12 carbon atoms, $R^1$ is a linear, branched or cyclic alkyl radical or an aryl radical having 2 to 8 carbon atoms and $R^2$ is a linear, branched or cyclic alkyl radical or an aryl radical or an oxyalkyl radical having 1 to 8 carbon atoms, where $C_{1-4}$-alkyl or phenyl radicals are preferred, and [Z] is a linear polyhydroxyalkyl radical whose alkyl chain is substituted by at least two hydroxyl groups, or alkoxylated, preferably ethoxylated or propoxylated, derivatives of this radical.

[Z] is preferably obtained by reductive amination of a reduced sugar, for example glucose, fructose, maltose, lactose, galactose, mannose or xylose. The N-alkoxy- or N-aryloxy-substituted compounds can then be converted into the desired polyhydroxy fatty acid amides, for example by reaction with fatty acid methyl esters in the presence of an alkoxide as catalyst.

In the preparation of the fine microparticles, suitable surfactants are in principle likewise any surfactants. However, for this intended use, preference is given to the above-described nonionic surfactants and here in particular to the low-foaming nonionic surfactants. Particular preference is given to the alkoxylated alcohols, particularly the ethoxylated and/or propoxylated alcohols. In this context, the person skilled in the art generally understands alkoxylated alcohols as meaning the reaction products of alkylene oxide, preferably ethylene oxide, with alcohols, preferably for the purposes of the present invention the longer-chain alcohols ($C_{10}$ to $C_{18}$, preferably between $C_{12}$ and $C_{16}$, such as, for example $C_{11}$-, $C_{12}$-, $C_{13}$-, $C_{14}$-, $C_{15}$-, $C_{16}$-, $C_{17}$-, and $C_{18}$-alcohols). Usually, n moles of ethylene oxide and one mole of alcohol produce a complex mixture of addition products of varying degree of ethoxylation, depending on the reaction conditions. A further embodiment consists in using mixtures of the alkylene oxides, preferably the mixture of ethylene oxide and propylene oxide. If desired, it is also possible, by means of a final etherification with short-chain alkyl groups, such as preferably the butyl group, to arrive at the class of substance of "closed" alcohol ethoxylates, which can likewise be used for the purposes of the invention. Very particular preference is given for the purposes of the present invention to highly ethoxylated fatty alcohols or mixtures thereof with terminally capped fatty alcohol ethoxylates.

Bleaches

The fine microparticles can also have bleaches. Among the compounds serving as bleaches which produce $H_2O_2$ in water, sodium perborate tetrahydrate and sodium perborate monohydrate are of particular importance. Further bleaches which can be used are, for example, sodium percarbonate, peroxypyrophosphates, citrate perhydrates and $H_2O_2$-producing peracidic salts or peracids, such as perbenzoates, peroxophthalates, diperazelaic acid, phthaloiminoperacid or diperdodecanedioic acid.

The content of bleaches in the washing and cleaning agents comprising fine particles is preferably 5 to 25% by weight and in particular 10 to 20% by weight, based on the total composition of the washing and cleaning agent, perborate monohydrate or percarbonate advantageously being used.

It is also possible when using the bleaches to dispense with the use of surfactants and/or builders, thereby making it possible to prepare pure, fine microparticles. If such bleaches are to be used for textile washing, preference is given to using sodium percarbonate, irrespective of which other ingredients are present in the washing and cleaning agents.

It is also possible to use bleaches from the group of organic bleaches for the preparation of the fine microparticles. Typical organic bleaches are the diacyl peroxides, such as, for example, dibenzoyl peroxide. Further typical organic bleaches are the peroxy acids, particular examples being the alkylperoxy acids and the arylperoxy acids. Preferred representatives are (a) the peroxybenzoic acid and its ring-substituted derivatives, such as alkylperoxybenzoic acids, but also peroxy-α-naphthoic acid and magnesium monoperphthalate, (b) aliphatic or substituted aliphatic peroxy acids, such as peroxylauric acid, peroxystearic acid, ε-phthalimidoperoxycaproic acid [phthaloiminoperoxy-hexanoic acid (PAP)], o-carboxybenzamidoperoxycaproic acid, N-nonenylamidoperadipic acid and N-nonenyl-amidopersuccinates, and (c) aliphatic and araliphatic peroxydicarboxylic acids, such as 1,12-diperoxy-carboxylic acid, 1,9-diperoxyazelaic acid, diperoxysebacic acid, diperoxybrassylic acid, the diperoxyphthalic acids, 2-decyldiperoxybutane-1, 4-dioic acid, N,N-terephthaloyldi(6-aminopercaproic acid) may be used for the preparation of the fine microparticles.

Bleaches which may be used in the fine microparticles are also substances which release chlorine or bromine. Among suitable chlorine- or bromine-releasing materials, examples include heterocyclic N-bromoamides and N-chloroamides, for example trichloroisocyanuric acid, tribromoisocyanuric acid, dibromoisocyanuric acid and/or dichloroisocyanuric acid (DICA) and/or salts thereof with cations such as potassium and sodium. Hydantoin compounds, such as 1,3-dichloro-5,5-dimethylhydantoin are likewise suitable.

Bleach Activators

In order to achieve an improved bleaching effect when washing or cleaning at temperatures of 60° C. and below, bleach activators may be present in the fine microparticles. Bleach activators which can be used for the preparation of the fine microparticles are compounds which, under perhydrolysis conditions, produce aliphatic peroxycarboxylic acids having preferably 1 to 10 carbon atoms, in particular 2 to 4 carbon atoms, and/or optionally substituted perbenzoic acid. Suitable substances are those which carry O- and/or N-acyl groups with said number of carbon atoms and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycolurile (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran.

In addition to the conventional bleach activators, or instead of them, it is also possible to use so-called bleaching catalysts in the preparation of the fine microparticles. These substances are bleach-boosting transition metal salts or transition metal complexes, such as, for example, Mn-, Fe-, Co-, Ru- or Mo-salen complexes or -carbonyl complexes. It is also possible to use Mn, Fe, Co, Ru, Mo, Ti, V and Cu complexes with N-containing tripod ligands, and also Co-, Fe-, Cu- and Ru-ammine complexes as bleach catalysts.

Bleach activators which can be used for the preparation of the fine microparticles are also the enol esters known from German patent applications DE-A-196 16 693 and DE-A-196 16 767, and also acetylated sorbitol and mannitol, or mixtures thereof described in European patent application EP-A-0 525 239 (SORMAN), acylated sugar derivatives, in particular pentaacetylglucose (PAG), pentaacetylfructose, tetraacetylxylose and octaacetyllactose, and acetylated, optionally N-alkylated glucamine and gluconolactone, and/or N-acylated lactams, for example N-benzoylcaprolactam, which are known from the International patent applications WO-A-94/27970, WO-A-94/28102, WO-A-94/28103, WO-A-95/00626, WO-A-95/14759 and WO-A-95/17498. The hydrophilically substituted acylacetals known from the German patent application DE-A-196 16 769 and the acyl-lactams described in German patent application DE-A-196 16 770 and International patent application WO-A-95/14075 are likewise preferably used for the preparation of the fine microparticles. The combinations of conventional bleach activators known from German patent application DE-A-44 43 177 can also be used for the preparation of the fine microparticles. Such bleach activators are present in the customary quantitative range, preferably in amounts of from 1% by weight to 10% by weight, in particular 2% by weight to 8% by weight, based on the total washing and cleaning agent having fine microparticles.

Particularly in the case of use in machine washing processes, it may be advantageous for customary foam inhibitors to be added to the fine microparticle agents. Examples of suitable foam inhibitors are soaps of natural or synthetic origin which have a high content of C18-C24-fatty acids. Suitable nonsurfactant-like foam inhibitors are, for example, organopolysiloxanes and mixtures thereof with microfine, optionally silanized, silica, and paraffins, waxes, microcrystalline waxes and mixtures thereof with silanized silica or bistearylethylenediamide. Mixtures of different foam inhibitors are also used with advantages, e.g. those of silicones, paraffins or waxes. The foam inhibitors, in particular silicone- and/or paraffin-containing foam inhibitors, are preferably bonded to a granular, water-soluble or -dispersible carrier substance. In particular, preference is given here to mixtures of paraffins and bistearylethylenediamides.

The fine microparticles can also have polyphosphonic acids as salts, preferably the neutrally reacting sodium salts of, for example, 1-hydroxyethane-1,1-diphosphonate, diethylenetriamine pentamethylenephosphonate or ethylenediamine tetramethylene-phosphonate in amounts of from 0.1 to 1.5% by weight, based on the total composition of the washing and cleaning agent comprising fine microparticles.

Enzymes

Suitable enzymes for the preparation of the fine microparticles are, in particular, those from the classes of hydrolases, such as the proteases, esterases, lipases or lipolytic enzymes, amylases, glycosyl hydrolases, and mixtures of said enzymes. All of these hydrolases contribute to the removal of soilings, such as proteinaceous, fatty or starchy stains. For bleaching, oxidoreductases can also be used. Particularly well suited for the preparation of the fine microparticles are those obtained from bacterial strains or fungi such as *Bacillus subtilis, Bacillus licheniformis, Streptomyceus griseus, Coprinus cinereus* and *Humicola insolens*, and enzymatic active ingredients obtained from their genetically modified variants. Preference is given to proteases of the Subtilisin type and in particular proteases which are obtained from *Bacillus lentus*. In this connection, enzyme mixtures, for example protease and amylase or protease and lipase or lipolytic enzymes or of protease, amylase and lipase or lipolytic enzymes or protease, lipase or lipolytic enzymes, but in particular protease and/or lipase-containing mixtures or mixtures with lipolytic enzymes are of particular interest. Examples of such lipolytic enzymes are the known cutinases. Peroxidases or oxidases have also proven suitable in some cases. Suitable amylases include, in particular, alpha-amylases, isoamylases, pullulanases and pectinases. Oxireductases are also suitable.

As well as the abovementioned enzymes, celluloses are also additionally suitable for the preparation of the fine microparticles. Cellulases and other glycosyl hydrolases can contribute, by removing pilling and microfibrils, to the retention of color and to an increase in the softness of the textile. The cellulases used are preferably cellobiohydrolases, endoglucanases and glucosidases, which are also called cellobiases, or mixtures thereof. Because different types of cellulase differ in their CMCase and Avicelase activities, specific mixtures of the cellulases may be used to establish the desired activities.

The enzymes can be adsorbed to carrier substances or embedded in coating substances in order to protect against premature decomposition. The proportion of the enzymes of enzyme mixtures can, for example, be about 0.1 to 5% by weight, preferably 0.5 to about 4.5% by weight, based on the washing and cleaning agent composition comprising fine microparticles.

Enzyme Stabilizers

In addition to phosphonates, the fine microparticles can also comprise further enzyme stabilizers. For example, the microparticles can comprise sodium formate. Also possible is the use of proteases which have been stabilized with soluble calcium salts and a calcium content of preferably about 1.2% by weight, based on the enzyme. Apart from calcium salts, magnesium salts also serve as stabilizers. However, of particular advantage is the use of boron compounds, for example of boric acid, boron oxide, borax and other alkali metal borates, such as the salts of orthoboric acid (H3BO3), of metaboric acid (HBO2) and of pyroboric acid (tetraboric acid H2B4O7).

Antiredeposition Agents

The fine microparticles can also comprise antiredeposition agents. Antiredeposition agents have the task of keeping the soil detached from the fiber suspended in the liquor and thus of preventing reattachment of the soiling. Suitable for this purpose are water-soluble colloids, usually organic in nature, for example the water-soluble salts of polymeric carboxylic acids, glue, gelatin, salts of ether carboxylic acids or ether sulfonic acids of starch or of cellulose, or salts of acidic sulfuric esters of cellulose or of starch. Water-soluble polyamides containing acidic groups are also suitable for this purpose. Furthermore, soluble starch preparations and starch products other than those mentioned above may be used, for example degraded starch, aldehyde starches etc. It is also possible to use polyvinylpyrrolidone. Preference, however, is given to the use of cellulose ethers, such as carboxymethylcellulose (Na salt), methylcellulose, hydroxyalkylcellulose and mixed ethers such as methylhydroxyethylcellulose, methylhydroxy-propylcellulose, methylcarboxymethylcellulose and mixtures thereof, and also polyvinylpyrrolidone, for example in amounts of from 0.1 to 5% by weight, based on the total composition of the washing and cleaning agent comprising fine microparticles.

Silver Protectants

According to the invention, for the preparation of the fine microparticles, in particular for machine washing and cleaning agents of dishes, corrosion inhibitors may be used to protect the ware or the machine, silver protectants being particularly important in the field of machine dishwashing. To prepare the fine microparticles, it is also possible to use the known substances of the prior art. Generally, for the preparation of the fine microparticles, use can be made primarily of silver protectants chosen from the group of triazoles, benzotriazoles, bisbenzotriazoles, aminotriazoles, alkylaminotriazoles and transition metal salts or transition metal complexes. For the preparation of the fine microparticles, particular preference is given to using benzotriazole and/or alkylaminotriazole. Moreover, washing and cleaning agents containing active chlorine are often found in cleaner formulations; these can significantly reduce corrosion of the silver surface, and they are also suitable for the preparation of the fine microparticles. In chlorine-free cleaners, for the preparation of the fine microparticles, use is made in particular of oxygen- and nitrogen-containing organic redox-active compounds, such as divalent and trivalent phenols, e.g. hydroquinone, pyrocatechol, hydroxyhydroquinone, gallic acid, phloroglucinol, pyrogallol, and derivatives of these classes of compound. Salt- and complex-like inorganic compounds, such as salts of the metals Mn, Ti, Zr, Hf, V, Co and Ce, can also be used for the preparation of the fine microparticles. For the preparation of the fine microparticles preference is given here to the transition metal salts which are chosen from the group of manganese and/or cobalt salts and/or complexes, particularly preferably the cobalt(ammine) complexes, the cobalt(acetate) complexes, the cobalt(carbonyl) complexes, the chlorides of cobalt or manganese and manganese sulfate. It is likewise possible to use zinc compounds to prevent corrosion on the ware for the preparation of the fine microparticles.

Soil-repelling Substances

Additionally, for the preparation of the fine microparticles, soil-repelling substances can also additionally be used which have a positive influence on the ability to wash oil and grease out of textiles (so-called soil repellents). This effect is particularly marked if a textile is soiled which has already been washed beforehand a number of times with a washing agent according to the invention which comprises this oil- and grease-dissolving component. Preferred oil- and grease-dissolving components for the preparation of the fine microparticles include, for example, nonionic cellulose ethers, such as methylcellulose and methylhydroxypropylcellulose with a proportion of methoxyl groups of from 15 to 30% by weight and of hydroxypropoxyl groups of from 1 to 15% by weight, in each case based on the nonionic cellulose ethers, and the polymers of phthalic acid and/or of terephthalic acid known from the prior art, and of derivatives thereof, in particular polymers of ethylene terephthalates and/or polyethylene glycol terephthalates or anionically and/or nonionically modified derivatives thereof. Of these, particular preference is given to the sulfonated derivatives of phthalic acid and of terephthalic acid polymers.

Optical Brighteners

These substances, which are also called "whiteners" are used for the preparation of the fine microparticles since even freshly washed and bleached white laundry has a slight yellow tinge. Optical brighteners are organic dyes which convert part of the invisible UV radiation of sunlight into longer-wave blue light. The emission of this blue light fills the "gap" in the light reflected by the textile, so that a textile treated with an optical brightener appears whiter and brighter to the eye. Since the mechanism of action of brighteners necessitates their attachment to the fibers, a distinction is made in accordance with the fibers "to be dyed" between, for example, brighteners for cotton, nylon or polyester fibers. The standard commercial brighteners suitable for the preparation of the fine microparticles belong essentially to five structural groups: the stilbene group, the diphenylstilbene group, the cumarin-quinoline group, the diphenylpyrazoline group and the group of the combination of benzoxazole or benzimidazole with conjugated systems. An overview of current brighteners can be found, for example, in G. Jakobi, A. Löhr "*Detergents and Textile Washing*", VCH-Verlag, Weinheim, 1987, pages 94 to 100. Examples of suitable brighteners are salts of 4,4'-bis[(4-anilino-6-morpholino-s-triazin-2-yl)amino]stilbene-2,2'-disulfonic acid or compounds with a similar structure which, instead of the morpholino group, carry a diethanolamino group, a methylamino group, an anilino group or a 2-methoxyethylamino group. In addition, brighteners of the substituted diphenylstryl type may be present, e.g. the alkali metal salts of 4,4'-bis (2-sulfostyryl)diphenyl, 4,4'-bis(4-chloro-3-sulfostyryl) diphenyl, or 4-(4-chlorostyryl)-4'-(2-sulfostyryl) diphenyl. Mixtures of the abovementioned brighteners may also be used.

Fragrances

Fragrances may be added to the [lacuna] for the preparation of the fine microparticles according to the invention in order to improve the aesthetic impression of the resulting washing and cleaning agents and to provide the consumer with not only the cleaning performance and the color impression, but also a sensorily "typical and unmistakable" washing and cleaning agent. As perfume oils or fragrances it is possible to use individual odorant compounds, e.g. the synthetic products of the ester, ether, aldehyde, ketone, alcohol and hydrocarbon type. Odorant compounds of the ester type are, for example, benzyl acetate, phenoxyethyl isobutyrate, p-tert-butylcyclohexyl acetate, linalyl acetate, dimethylbenzyl-carbinyl acetate, phenylethyl acetate, linalyl benzoate, benzyl formate, ethyl methylphenylglycinate, allyl cyclohexylpropi-onate, styrallyl propionate, and benzyl salicylate. The ethers include, for example, benzyl ethyl ether; the aldehydes include, for example, the linear alkanals having 8-18 carbon atoms, citral, citronellal, citronellyloxyacetaldehyde, cycla-men aldehyde, hydroxycitronellal, lilial and bourgeonal; the ketones include, for example, the ionones, α-isomethylion-one and methyl cedryl ketone; the alcohols include anethol, citronellol, eugenol, geraniol, linalool, phenylethyl alcohol, and terpeneol; the hydrocarbons include primarily the terpenes such as limonene and pinene. Preference is, however, given to using mixtures of different odorants for the preparation of the fine microparticles according to the invention which together produce a pleasing scent note. Such perfume oils may also comprise natural odorant mixtures, as are obtainable from plant sources, examples being pine oil, citrus oil, jasmine oil, patchouli oil, rose oil or ylang ylang oil. Likewise suitable are muscatel, sage oil, camomile oil, oil of cloves, balm oil, mint oil, cinnamon leaf oil, lime blossom oil, juniper berry oil, vetiver oil, olibanum oil, galbanum oil and labdanum oil, and also orange blossom oil, neroliol, orange peel oil and sandalwood oil.

The fragrances can be incorporated directly into the fine microparticle, although it may also be advantageous to apply the fragrances to the fine microparticles. This achieves improved adhesion of the perfume to the laundry. Furthermore, slower scent release for long-lasting scent of the washing and cleaning agent and of the treated textiles is achieved.

Those carrier materials which have proven suitable for the preparation of the fine microparticles according to the invention are, for example, cyclodextrins, where the cyclodextrin perfume complexes can also additionally be coated with further auxiliaries.

Disintegration Auxiliaries

In order to facilitate disintegration of the fine microparticles, it is possible to incorporate disintegration auxiliaries, so-called tablet disintegrants, into them in order to shorten the disintegration times. Tablet disintegrants or disintegration accelerators are, according to Römpp (9$^{th}$ edition, Vol. 6, p. 4440) and Voigt "Lehrbuch der pharmazeutischen Technologie" [Textbook of Pharmaceutical Technology] (6$^{th}$ edition, 1987, pp. 182-184), understood as meaning auxiliaries which ensure the rapid disintegration of tablets in water or gastric fluid and the release of the drugs in absorbable form.

These substances, which, due to their effect, are also referred to as disintegrants, increase in volume upon ingress of water, with on the one hand an increase in the intrinsic volume (swelling) and on the other hand, by way of the release of gases as well, the possibility of generating a pressure which causes the tablet to disintegrate into smaller particles. Examples of established disintegration auxiliaries are carbonate/citric acid systems, with the use of other organic acids also being possible. Examples of swelling disintegration auxiliaries are synthetic polymers such as polyvinylpyrrolidone (PVP) or natural polymers or modified natural substances such as cellulose and starch and their derivatives, alginates, or casein derivatives.

Preferred washing and cleaning agents having fine microparticles comprise 0.5 to 10% by weight, preferably 3 to 7% by weight and in particular 4 to 6% by weight, of one or more disintegration auxiliaries, in each case based on the washing and cleaning agent weight.

For the purposes of the present invention, preferred disintegration agents which are suitable for the preparation of the fine microparticles according to the invention are disintegration agents based on cellulose, so that preferred washing and cleaning agents having fine microparticles comprise such a cellulose-based disintegration agent in amounts of from 0.5 to 10% by weight, preferably 3 to 7% by weight and in particular 4 to 6% by weight. Pure cellulose has the formal net composition $(C_6H_{10}O_5)_n$ and, when considered formally, represents a β-1,4-polyacetal of cellobiose, which in turn is constructed from two molecules of glucose.

Suitable celluloses consist here of about 500 to 5 000 glucose units and accordingly have average molar masses of from 50 000 to 500 000. Cellulose-based disintegration agents which can be used for the purposes of the present invention are also cellulose derivatives which are available by polymer-analogous reactions from cellulose. Such chemically modified celluloses include, for example, products of esterifications or etherifications in which hydroxy hydrogen atoms have been substituted. However, celluloses in which the hydroxy groups have been replaced by functional groups which are not bonded via an oxygen atom can also be used as cellulose derivatives. The group of cellulose derivatives includes, for example, alkali metal celluloses, carboxymethylcellulose (CMC), cellulose esters and ethers, and amino-celluloses. Said cellulose derivatives are preferably not used alone as cellulose-based disintegration agents, but are used in a mixture with cellulose. The content of cellulose derivatives in these mixtures is preferably less than 50% by weight, particularly preferably less than 20% by weight, based on the cellulose-based disintegration agent. As cellulose-based disintegration agent, particular preference is given to using pure cellulose which is free from cellulose derivatives for the preparation of the fine microparticles according to the invention.

A further cellulose-based disintegration agent which can be used for the preparation of the fine microparticles according to the invention is microcrystalline cellulose. This microcrystalline cellulose is obtained by partial hydrolysis of celluloses under conditions which attack and completely dissolve only the amorphous regions (about 30% of the total cellulose mass) of the celluloses, but leave the crystalline regions (about 70%) undamaged.

Dyes

In order to improve the aesthetic impression of the washing and cleaning agents according to the invention, the fine microparticles can be formed from dyes or be colored with suitable dyes, preference being given to the brightener-containing phase(s) comprising the total amount of dye(s). Preferred dyes, the selection of which does not present the person skilled in the art with any problem, have a high storage stability and insensitivity toward the other ingredients of the washing and cleaning agent and toward light and also no marked substantivity toward textile fibers, in order not to color these.

For the preparation of the fine microparticles according to the invention, preference is given to all colorants which can be oxidatively destroyed in the washing process, and to mixtures thereof with suitable blue dyes, so-called bluing agents. It has proven advantageous to use colorants for the preparation of the fine microparticles according to the invention which are soluble in water or at room temperature in liquid organic substances. Examples of suitable colorants are anionic colorants, e.g. anionic nitroso dyes. One possible colorant is, for example, naphthol green (Colour Index (CI) Part 1: Acid Green 1; Part 2: 10020), which, being a commercial product, is available, for example, as Basacid® Green 970 from BASF, Ludwigshafen, and also mixtures of this with suitable blue dyes. Further suitable colorants are Pigmosol® Blue 6900 (CI 74160), Pigmosol® Green 8730 (CI 74260), Basonyl® Red 545 FL (CI 45170), Sandolan® RhodaminEB400 (CI 45100), Basacid® Yellow 094 (CI 47005), Sicovit® Patent Blue 85 E 131 (CI 42051), Acid Blue 183 (CAS 12217-22-0, CI Acid Blue 183), Pigment Blue 15 (CI 74160), Supranol® Blue GLW (CAS 12219-32-8, CI Acid Blue 221), Nylosane® Yellow N-7GL SGR (CAS 61814-57-1, CI Acid Yellow 218) and/or Sandolan® Blue (CI Acid Blue 182, CAS 12219-26-0).

When choosing the colorant, it must be ensured that the colorants do not have too great an affinity toward the textile surfaces, and especially toward synthetic fibers. At the same time, it should also be borne in mind when choosing suitable colorants that colorants have different stabilities with respect to oxidation. The general rule is that water-insoluble colorants are more stable toward oxidation than water-soluble colorants. Depending on the solubility and thus also on the oxidation sensitivity, the concentration of the colorant in the washing and cleaning agents varies. With readily water-soluble colorants, e.g. the abovementioned Basacid® Green or the likewise abovementioned Sandolan® Blue, colorant concentrations chosen are typically in the range from a few $10^{-2}$ to $10^{-3}$% by weight, in each case based on the total washing and cleaning agent. In the case of the pigment dyes, which are particularly preferred due to their brilliance but are less readily soluble in water, for example the abovementioned Pigmosol® dyes, the suitable concentration of the colorant in washing or cleaning agents is, in contrast, typically from a few $10^{-3}$ to $10^{-4}$% by weight, based on the total washing and cleaning agent. Since the dyes are preferably used in one phase, i.e. a relatively small section of the shaped body, the content of dyes in the phase can be much higher.

Fine microparticles can be prepared, for example, by grinding, it being possible, in air-jet mills to obtain microparticle sizes of less than 10 µm. For yet smaller microparticles, such as nanoparticles, the processes known in the prior art can be used.

Further suitable processes for the preparation of the fine microparticles, in particular of nanoparticles, are listed below:

Crystallization Process

This process is a crystallization from solutions with considerable supersaturation in order to produce as many crystal germs as possible. In this connection, the supersaturation must be uniformly high as far as possible throughout the entire medium in which crystallization takes place so that many germs for a finely divided crystallizate are produced on virtually all sites. The supersaturation from solutions can be established, for example, by severe cooling of the solvent, by abrupt evaporation of the solvent, by very rapid addition of an antisolvent or a displacing other substance, e.g. addition of salt, by changing the pH or the like, depending on the solubility behavior of the substance to be obtained. Suitable processes whose principle of crystallization are based on a high degree of supersaturation, include spraying processes, such as spray-drying, spraying into an antisolvent, see WO 90/03782 to which reference is made in its entirety, and spraying processes with simultaneous cooling (Direct Contact Cooling).

Solidification from Sprayed Melt

In this process, the fine microparticles according to the invention are achieved through a correspondingly fine atomization of the melt, where the fine microparticles have to solidify first before a reagglomeration can take place, e.g. Jet Priller from GMF Gouda.

For example using the PGSS process, see EP 0744992, to which reference is made here in its entirety (?), a cooling, solidification and solvent vaporization in a [lacuna] to give the fine microparticles according to the invention is possible.

Precipitation Reactions

Here, reactions are carried out in solutions, where the reaction product, in contrast to the starting materials, is insoluble or only slightly soluble in the solution medium. This results in a very considerable supersaturation locally, which leads to correspondingly finely divided crystallized product. This is also particularly effective as a spray process—"spray conversion process".

Fine microparticles according to the invention in the nanoparticle range can be generated by reactive conversion also in the bulk phase, a fine distribution of a reactant often being carried out prior to the reaction—e.g. coaservation with prior dispersion in the case of microencapsulation; fine grinding of a metallic precursor in a carrier medium in the case of the preparation of ceramic powders.

The process suitable in each case for the preparation of the fine microparticles should be selected depending on the washing agent constituent used, for example fragrance and/or surfactant.

The fine surfactant and perfume microparticles can preferably be used in three supply forms:
- as pure substance particles
- as microcompound on a likewise finely divided carrier
- as very fine microparticles (solid or as drops) in a relatively large carrier matrix.

Examples 1 and 3 are comparative examples. By contrast, Example 2 relates to a washing and cleaning agent composition with fine microparticles according to the invention.

EXAMPLE 1

Washing agent extrudate with a high perfume oil content

| Formulation 1: | |
|---|---|
| Surfactant granulate | 75.00% |
| PEG 4000 | 4.00% |
| Zeolite A | 15.00% |
| Perfume oil | 6.00% |
| Surfactant granulate: | |
| $C_{9-13}$-alkylbenzenesulfonate | 15.4% |
| $C_{12-18}$-fatty alcohol sulfate | 6.7% |
| Soap | 1.6% |

-continued

| Formulation 1: | |
|---|---|
| Sodium carbonate | 22.9% |
| Zeolite A | 45% |
| Na hydroxyethane-1,1-diphosphonate | 1.6% |
| Acrylic acid-maleic acid copolymer | 5.5% |
| Water, salts | 1.3% |

The solid constituents are premixed in a mixer (Lödige plow-share mixer), during which the perfume oil is added in liquid form.

After the mixing, the premix was processed in a double-screw extruder to give extrudates (diameter: 1.4 mm). This gave a flowable extrudate, the dissolution behavior of which was investigated using the L-test.

Residue Determination (L-test):
 1 000 ml of tap water are placed in a 2 000 ml beaker at 30° C.;
 switch on the stirrer at the designated stirrer speed;
 scattering in the fixed amount of the washing agent to be tested and stir for 90 seconds (stopwatch);
 then immediately pour the wash liquor through a sieve (handwash test);
 then dry the sieve in the drying cabinet at 40° C. to a constant weight; and
 weigh the washing agent residue.

EXAMPLE 2

Washing agent extrudate with a high perfume oil content

| Formulation 2: | |
|---|---|
| Surfactant granulate | 66.00% |
| PEG 4000 | 4.00% |
| Zeolite A | 15.00% |
| Perfume compound | 15.00% |

Composition of the surfactant granulate as in Formulation 1.

The perfume compound comprises 40% perfume oil. In the overall formulation, this thus gives a perfume oil content of 6%, as in Formulation 1. The perfume compound was present here as fine microparticle, with a particle size $x_{90}=25$ μm. Zeolite A, acrylic acid-maleic acid copolymer and cyclodextrin were used as carrier material.

All of the formulation constituents were processed in a Lödige mixer to give a premix, the perfume oil being added to the premix not as in the case of Formulation 1 as a pure liquid, but in the form of fine microparticles. The fine microparticles with the abovementioned particle size comprised carrier substance and perfume oil, the perfume oil was thus present in the premix in microparticulate form.

The further processing of the premix was carried out as for Formulation 1. Following the extrusion, shaped bodies compacted in this way comprising fine perfume oil-containing microparticles were obtained.

This gave a flowable extrudate, the dissolution behavior of which was investigated using the L-test.

EXAMPLE 3

Washing agent extrudate with a high perfume oil content

| Formulation 3: | |
|---|---|
| Surfactant granulate | 66.00% |
| PEG 4000 | 4.00% |
| Zeolite A | 15.00% |
| Compound material without perfume oil | 9% |
| Perfume oil | 6.00% |

The composition of the surfactant granulate is the same as in Formulation 1.

The compound material corresponds to the carrier material of the perfume compound from Formulation 2, but without perfume oil.

Perfume oil was added, as in Formulation 1, to the mixer as a liquid.

The further processing of the premix was carried out as for Formulation 1.

This gave a flowable extrudate, the dissolution behavior of which was investigated using the L-test.

| Comparison of the L-test values of the extrudates: | |
|---|---|
| | L-test residue |
| Example 1 Extrudates as in Formulation 1 (comparison) | 25% |
| Example 2 Extrudates as in Formulation 2 (according to the invention) | 12% |
| Example 3 Extrudates as in Formulation 3 (comparison) | 27% |

As can be seen from the results, the dissolution or dispersion behavior for Formulation 2 (Example 2) is significantly more favorable than that for Formulation 1 and 3. The differences arise not from the differing formulation proportions (Formulation 2 versus Formulation 1), but from the nature of the raw material formulation of the perfume oil (compare Formulation 2—fine microparticles—versus Formulation 3). Replacing surfactant granulate with carrier compound without perfume oil (Formulation 3 versus Formulation 1) has only a slight influence on the dispersion behavior within the framework under consideration.

What is claimed:

1. A washing and cleaning agent shaped body that is silicone-free and is in the form of a granulate, extrudate, agglomerate, or tablet, said body comprising fine fragrance microparticles that are not coated, but instead are absorbed or adsorbed on a carrier material, wherein the carrier material is selected from the group consisting of starch compounds, silicates and mixtures thereof, and the microparticles enter into solution during the washing process and actively participate in the cleaning process, wherein the fine microparticles have a particle size distribution of 0.5 μm to 1 μm and 0.5 to 10% by weight of one or more disintegration auxiliaries.

2. The washing and cleaning agent shaped body of claim 1, wherein the fragrance is present in the fine microparticles in gel, solid, and/or liquid form.

3. The washing and cleaning agent shaped body of claim 1, comprising 0.01% to 90% by weight of the fine microparticles, based on the total composition of the shaped body.

4. The washing and cleaning agent shaped body of claim 3, comprising 0.1% to 70% by weight of the fine microparticles, based on the total composition of the shaped body.

5. The washing and cleaning agent shaped body of claim 4, comprising 0.1% to 10% by weight of the fine microparticles, based on the total composition of the shaped body.

6. The washing and cleaning agent shaped body of claim 4, comprising 1% to 60% by weight of the fine microparticles, based on the total composition of the shaped body.

7. The washing and cleaning agent shaped body of claim 6, comprising 10% to 50% by weight of the fine microparticles, based on the total composition of the shaped body.

8. The washing and cleaning agent shaped body of claim 7, comprising 20% to 40% by weight of the fine microparticles, based on the total composition of the shaped body.

9. The washing and cleaning agent shaped body of claim 1, wherein the microparticles comprise up to 100% by weight of one or more fragrance components.

10. The washing and cleaning agent shaped body of claim 9, wherein the microparticles comprise 1% to 90% by weight of the one or more fragrance components.

11. The washing and cleaning agent shaped body of claim 10, wherein the microparticles comprise 5% to 70% by weight of the one or more fragrance components.

12. The washing and cleaning agent shaped body of claim 11, wherein the microparticles comprise 10% to 60% by weight of the one or more fragrance components.

13. The washing and cleaning agent shaped body of claim 12, wherein the microparticles comprise 20% to 50% by weight of the one or more fragrance components.

14. The washing and cleaning agent shaped body of claim 13, wherein the microparticles comprise 30% to 40% by weight of the one or more fragrance components.

15. The washing and cleaning agent shaped body of claim 1, wherein individual microparticles have identical or different compositions of one or more fragrance components.

16. A process for the preparation of washing and cleaning agent shaped bodies that are silicone-free, comprising the steps of forming fine fragrance microparticles that are not coated, but instead are absorbed or adsorbed on a carrier material, wherein the carrier material is selected from the group consisting of starch compounds, silicates, and mixtures thereof, wherein said microparticles enter into solution during the washing process and actively participate in the cleaning process and subjecting the fine microparticles to a mechanical compaction process to form the shaped bodies, wherein the fine particles have a particle size distribution of 0.5 μm to 1 μm and 0.5 to 10% by weight of one or more disintegration auxiliaries.

17. A washing and cleaning agent shaped body that is silicone-free and is in the form of a granulate, extrudate, agglomerate, or tablet, said body comprising fine fragrance microparticles that are not coated but instead are absorbed or adsorbed on a carrier material, wherein the carrier material is selected from the group consisting of starch compounds, silicates, and mixtures thereof, and the microparticles enter into solution during the washing process and actively participate in the cleaning process, wherein the fine microparticles have a particle size of ≦2 μm.

18. The washing and cleaning agent shaped body of claim 17, wherein the fine microparticles have a particle size of ≦1 μm.

19. The washing and cleaning agent shaped body of claim 17, wherein the fine microparticles have a particle size of ≦0.5 μm.

20. The washing and cleaning agent shaped body of claim 17, wherein the fine microparticles have a particle size of 0.1 μm.

21. The washing and cleaning agent shaped body of claim 17, wherein the fragrance is present in the fine microparticles in gel, solid, and/or liquid form.

22. The washing and cleaning agent shaped body of claim 17, comprising 0.01% to 90% by weight of the fine microparticles, based on the total composition of the shaped body.

23. The washing and cleaning agent shaped body of claim 22, comprising 0.1% to 70% by weight of the fine microparticles, based on the total composition of the shaped body.

24. The washing and cleaning agent shaped body of claim 23, comprising 0.1% to 10% by weight of the fine microparticles, based on the total composition of the shaped body.

25. The washing and cleaning agent shaped body of claim 23, comprising 10% to 50% by weight of the fine microparticles, based on the total composition of the shaped body.

26. The washing and cleaning agent shaped body of claim 25, comprising 20% to 40% by weight of the fine microparticles, based on the total composition of the shaped body.

27. The washing and cleaning agent shaped body of claim 17, wherein the microparticles comprise up to 100% by weight of one or more fragrance components.

28. The washing and cleaning agent shaped body of claim 27, wherein the microparticles comprise 1% to 90% by weight of the one or more fragrance components.

29. The washing and cleaning agent shaped body of claim 28, wherein the microparticles comprise 10% to 60% by weight of the one or more fragrance components.

30. The washing and cleaning agent shaped body of claim 17, wherein individual microparticles have identical or different compositions of one or more fragrance components.

31. A process for the preparation of washing and cleaning agent shaped bodies that are silicone-free, comprising the steps of forming fine fragrance particles that are not coated, but instead are absorbed or adsorbed on a carrier material, wherein the carrier material is selected from the group consisting of starch compounds, silicates, and mixtures thereof, wherein said microparticles enter into solution during the washing process and actively participate in the cleaning process and subjecting the fine microparticles to a mechanical compaction process to form the shaped bodies, wherein the fine particles have a particle size of ≦2 μm.

32. A washing and cleaning agent shaped body that is silicone-free and is in the form of a granulate, extrudate, agglomerate, or tablet, said body comprising microparticles that comprise fine fragrance and surfactant that are not coated, but instead are both absorbed or absorbed on a carrier material, wherein the carrier material is selected from the group consisting of starch compounds, natural and synthetic polymers, silicates and silicas and mixtures thereof, and the microparticles enter into solution during the washing process and actively participate in the cleaning process, wherein the fine microparticles have a particle size distribution of 0.5 μm to 1 μm and 0.5 to 10% by weight of one or more disintegration auxiliaries.

* * * * *